United States Patent [19]

Chen

[11] 4,078,022
[45] Mar. 7, 1978

[54] 5-NORBORNENE-2-METHYL PHOSPHITES AND PHOSPHATE

[75] Inventor: Mark Chaoming Chen, Wilmington, Del.

[73] Assignee: E. I. Du Pont de Nemours and Company, Wilmington, Del.

[21] Appl. No.: 698,017

[22] Filed: Jun. 21, 1976

[51] Int. Cl.$^2$ .................. C07F 9/117; C07F 9/144; C08K 5/53

[52] U.S. Cl. .................. 260/956; 260/5; 260/45.7 P; 260/45.7 PH

[58] Field of Search .................. 260/956, 963, 967

[56] References Cited

U.S. PATENT DOCUMENTS 2,767,206   10/1956   Whetstone et al. .................. 260/956

*Primary Examiner*—Anton H. Sutto

[57] ABSTRACT

Bis(5-norbornene-2-methyl) phosphite, tris(5-norbornene-2-methyl) phosphite, and tris(5-norbornene-2-methyl) phosphate, as well as a mixture of the above esters are novel compositions of matter, useful as antiozonants in chloroprene polymers and in blends of chloroprene polymers with diene rubbers.

8 Claims, No Drawings

5-NORBORNENE-2-METHYL PHOSPHITES AND PHOSPHATE

BACKGROUND OF THE INVENTION

This invention relates to certain phosphite and phosphate esters of 5-norbornene-2-methanol which are useful as antiozonants in chloroprene polymers.

Although elastomeric chloroprene polymers are exceptionally resistant to attack by atmospheric ozone, it is desirable for certain applications (such as, for example, flexing or stretching at elevated temperatures) to further reduce their ozone susceptibility. U.S. Pat. No. 3,563,947 to Gruber discloses a class of 5-norbornen-2-yl compounds having high antiozonant activity in such applications.

A class of hexachloronorbornenylmethyl phosphates has recently been disclosed in German Offenlegungschrift No. 2,243,006. Those compounds are useful as flame retardants for plastics.

While the synthesis of most phosphorus acid esters is quite simple, side reactions occassionally complicate the preparation of some of them. This is especially so in the case of trivalent phosphorus compounds, which frequently undergo spontaneous oxidation to pentavalent phosphorus compounds when the reaction is carried out in the presence of air.

SUMMARY OF THE INVENTION

According to the present invention, there is now provided a new class of phosphites and phosphates of 5-norbornene-2-methanol which are very good antiozonants in chloroprene polymers. Mixtures of such esters also are effective antiozonants. The specific esters are:

(1) bis(5-norbornene-2-methyl) phosphite;
(2) tris(5-norbornene-2-methyl) phosphite; and
(3) tris(5-norbornene-2-methyl) phosphate.

DETAILED DESCRIPTION OF THE INVENTION

The 5-norbornene-2-methyl radical can be represented by the following formula:

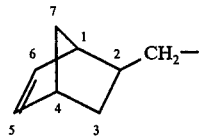

wherein CH groups are present in all positions except 3 and 7, and $CH_2$ groups are present in positions 3 and 7.

The above esters are made by conventional synthetic methods but are difficult to isolate in a pure state. General methods of synthesis, suitable for the preparation of the above compounds, are described, for example, in "Organic Phosphorus Compounds" edited by G. M. Kosolapoff and L. Maier, Wiley-Interscience, New York, N.Y. 1973. Of particular interest are chapters entitled "Organic Derivatives of Phosphorous Acid and Thiophosphorous Acid" by W. Gerrard and H. R. Hudson in Vol. 5 and "Organic Derivatives of Phosphoric Acid" by E. Cherbuliez in Vol. 6.

Tris(5-norbornene-2-methyl) phosphite could not be prepared by reaction of 5-norbornene-2-methanol with phosphorus trichloride in the absence of base, the major product being bis(5-norbornene-2-methyl) phosphite. A reaction of phosphorus oxychloride with 5-norbornene-2-methanol gave a good yield of the expected tris(5-norbornene-2-methyl) phosphate. Transesterification of triphenyl phosphite with sodium 5-norbornene-2-methoxide gave a product mixture containing tris(5-norbornene-2-methyl) phosphite as its major component. While each method results in a mixture of all three products, usually also containing some 5-norbornene-2-methanol, the mixtures obtained from the phosphorus trichloride reaction requires more careful purification because residual hydrochloric acid decreases the storage stability of the product mixture with concommitant decrease of antiozonant activity.

Because of the difficulty of isolation and purification of the esters of the present invention, their identification was based principally not on elemental analysis but on infrared spectroscopy combined with mass spectroscopy. The analytical samples were first isolated by gas chromatography.

It is apparent that depending on the particular technique used, the proportions of the various components of the product mixture will vary. Since, however, each of the esters in the mixture has antiozonant properties, it is not necessary for practical purposes to isolate any particular ester from the mixture. Usually, mixtures of bis(5-norbornene-2-methyl) phosphite, tris(5-norbornene-2-methyl) phosphite, tris(5-norbornene-2-methyl) phosphate, and 5-norbornene-2-methanol containing about 30–70 weight percent of tris(5-norbornene-2-methyl) phosphite are obtained by the $PCl_3$-base method. Those mixtures, especially those wherein the proportion of tris(5-norbornene-2-methyl) phosphite is at least 40 weight percent, are valuable antiozonants.

This invention is now illustrated by the following examples of certain preferred embodiments thereof, where all parts, proportions and percentages are by weight unless otherwise indicated.

Analytical Techniques

The gas chromatographic analyses in the following examples were made using a Hewlett Packard 5750 chromatograph, detector, and a 1 mv recorder. The 304-stainless steel column contained a silicone oil (OV-1, available from Supelco, Bellefonte, Pa.) partitioning liquid on a Chromsorb W-HP (Celite Div., Johns-Manville Product Corp.) support. The injection port was at 250° C., the detector at 350° C., the carrier gas argon, and the column temperature was programmed from 90° C. at 10° C./min. to 250° C. and hold.

The gas chromatograph was directly coupled to a mass spectrometer in such a manner that any chemical compound whose peak appeared on the gas chromatogram could be swept directly into the ionization chamber of the mass spectrometer, where its molecular ion weight was determined. Either a Hewlett-Packard G.C.-mass spectrometer Model 5981A or Du Pont G.C.-mass spectrometer Model 491 with chemical ionization source was used.

EXAMPLE 1

Bis(5-Norbornene-2-Methyl) Phosphite

A mixture of 372 g of 5-norbornene-2-methanol and 303 g triethylamine was slowly added with vigorous agitation to a solution of 206 g of phosphorus trichloride in 700 ml of benzene at 0° C. The addition was made at such a rate that the temperature of the reaction mixture did not exceed 2° C. The addition took 4 hours. The temperature of the reaction mixture was then raised to 25° C. and a further 193 g of 5-norbornene-2-methanol added. After standing about 16 hours at room temperature, the reaction mixture was filtered, and the filtrate was extracted with 250 ml water and dried over sodium sulfate. After removal of volatiles there was obtained 401.3 g product.

A gas chromatogram of the product showed two major peaks with an area ratio of 30:70. The product was vacuum distilled to give a fraction of b.p. 157°–160° C. (0.5 mm Hg). This fraction contained two major peaks with an area ratio of 8:91.

The infrared (IR) spectrum of the fraction exhibited the following bands:

| Weak OH | 3350 cm$^{-1}$ |
|---|---|
| P—H | 2420 cm$^{-1}$ |
| P=O | 1270 cm$^{-1}$ |
| P-O-C | 970 cm$^{-1}$ |
| Norbornene | 770 cm$^{-1}$ |

The IR spectrum of 5-norbornene-2-methanol showed a strong OH band (3350 cm$^{-1}$) and a strong band at 770 cm$^{-1}$ but no P—H or P=O bands.

The molecular ion (M$^+$) of the second peak of the gas chromatogram had MW = 294, which agreed with the calculated molecular weight of bis(5-norbornene-2-methyl) phosphite ($C_{16}H_{23}O_3P$).

Assuming that chromatogram peak area ratios roughly correspond to weight ratios, the fraction contained 8% 5-norbornene-2-methanol and 91% bis(5-norbornene-2-methyl) phosphite.

EXAMPLE 2

Tris(5-Norbornene-2-Methyl) Phosphate

5-Norbornene-2-methanol (186 g), 130 g of pyridine, and 300 ml of benzene were added to a one-liter flask equipped with a reflux condenser protected by a calcium chloride drying tube, a mechanical stirrer, a dropping funnel, and a thermometer. The mixture was cooled to about 0° C. A solution of 76.5 g of phosphorus oxychloride in 50 ml of benzene was added dropwise with stirring over a period of two hours. The reaction mixture temperature was kept at 30° C. or lower by external cooling. After the addition, the reaction mixture was stirred for 30 minutes at about 30° C., and then heated at reflux for 2 hours. After cooling, precipitated pyridine hydrochloride was removed by filtration, and the precipitate was washed with 50 ml of benzene. The combined filtrate and washing were washed twice with 250-ml. portions of cold water and then dried over anhydrous sodium sulfate. Solvent was removed under vacuum and the resulting product analyzed.

An IR spectrum of the product showed the following absorptions:

| Weak OH | 3350 cm$^{-1}$ |
|---|---|
| P=O | 1270 cm$^{-1}$ |
| P-O-C | 1010 cm$^{-1}$ |
| Norbornene | 770 cm$^{-1}$ |

A gas chromatogram gave a major peak of 95% of total peak area. The molecular ion of the major peak had MW = 416, the same as the calculated molecular weight of tris(5-norbornene-2-methyl) phosphate ($C_{24}H_{33}O_4P$); two other small peaks were identified as 5-norbornene-2-methanol (0.42% of total peak area) and tris(5-norbornene-2-methyl) phosphite (0.82% of total peak area).

EXAMPLE 3

Bis(5-Norbornene-2-Methyl) Phosphite, Tris(5-Norbornene-2-Methyl) Phosphite, Tris(5-Norbornene-2-Methyl) Phosphate Mixture A. A mixture of 0.3 g of sodium and 314 g of 5-norbornene-2-methanol was allowed to react at 80° C. for about three hours under a nitrogen atmosphere. The solution was then cooled to room temperature, and 261.5 g of triphenyl phosphite was added. The reaction mixture was stirred at room temperature for about 15 hours under a nitrogen atmosphere. Removal of volatiles gave a 331.0 g residue.

A gas chromatogram of the residue showed three peaks having retention times corresponding to 5-norbornene-2-methanol, bis(5-norbornene-2-methyl) phosphite and tris(5-norbornene-2-methyl) phosphate. A fourth peak having a retention time between those of bis(5-norbornene-2-methyl) phosphite and tris(5-norbornene-2-methyl) phosphate gave a molecular ion of MW = 400, consistent with that of tris(5-norbornene-2-methyl) phosphite ($C_{24}H_{33}O_3P$). Additional peaks, attributable to other compounds of the mixture, also were observed.

The following quantitative relationships were determined by gas chromatography:

5-norbornene-2-methanol — 13.9 area %
bis(5-norbornene-2-methyl) phosphite — 29.5 area %
tris(5-norbornene-2-methyl) phosphite — 41.1 area %
tris(5-norbornene-2-methyl) phosphate — 3.3 area %

The IR spectrum of the residue gave absorptions corresponding to OH, P—H, P=O, P—O—C and norbornene.

B. A mixture of 0.5 g sodium and 1000 g 5-norbornene-2-methanol was allowed to react at 80° C. for about 3 hours under a nitrogen atmosphere. The solution was cooled to about 50° C., and 686 g of triphenyl phosphite was added. After the addition, the mixture was heated at 100° C. for about 15 hours. Volatiles, consisting primarily of excess 5-norbornene-2-methanol and phenol, were removed under vacuum, and the resulting crude product, 864.3 g, was treated with 54 g of activated charcoal. The resulting product, 815.6 g, was shown by gas chromatography to have the following composition:

5-norbornene-2-methanol — 5.8 area %
bis(5-norbornene-2-methyl) phosphite — 15.9 area %
tris(5-norbornene-2-methyl) phosphite — 65.5 area %
tris(5-norbornene-2-methyl) phosphate — 0.7 area %

Additional peaks were observed by gas chromatography but were not identified.

EXAMPLE 4

Tris(5-norbornene-2-methyl) Phosphite

Sodium metal (0.5 g) was dissolved at an elevated temperature in 1000 g of freshly distilled 5-norbornene-2-methanol under a nitrogen atmosphere. The solution was cooled to room temperature, and 686 g triphenylphosphite was added. The mixture was heated to 100° C. for 36 hours. Excess 5-norbornene-2-methanol and by-product phenol were removed by vacuum distillation. The viscous off-white liquid residue (863.3 g) was added to 50 parts decolorizing carbon ("Norit" A, product of American Norit Co.) and stirred at room temperature for one hour. After removal of the black by filtration under nitrogen, 811.2 g of a liquid were recovered. A 128.8 g portion of the liquid was distilled and the following three fractions collected:

Fraction I:18.6 g, b.p. 185°–199° C./0.30–0.68 mmHg.
Fraction II:42.5 g, b.p. 194°–196° C./0.45–0.60 mmHg.
Fraction III:59.5 g, b.p. 195°–197° C./0.45–0.60 mmHg.

Gas chromatographic analyses determined that the fractions contained, respectively, 79, 81 and 83 area % tris(5-norbornene-2-methyl) phosphite.

EXAMPLE 5

The Use of Bis(5-Norbornene-2-Methyl) Phosphite, Tris(5-Norbornene-2-Methyl) Phosphate, and Their Mixture With Tris(5-Norbornene-2-Methyl) Phosphite as Antiozonants Four samples of a neoprene-natural rubber compound containing the following ingredients were prepared by standard rubber mixing techniques.

| | | |
|---|---|---|
| Neoprene[a] | 50 | parts |
| Pale Crepe Natural Rubber | 50 | |
| Semi-Reinforcing Carbon Black | 30 | |
| Naphthenic Oil[b] | 10 | |
| Stearic Acid | 2 | |
| Antioxidant[c] | 2 | |
| Zinc Oxide | 5 | |
| N-Cyclohexyl-2-Benzothiazyl Sulphenamide[d] | 0.6 | |
| Diphenylguanidine | 0.3 | |
| Sulfur | 1.3 | |
| Antiozant | As Shown in Table I | |

[a]A mercaptan-modified chloroprene polymer prepared by polymerizing 100 parts of chloroprene in an aqueous, alkaline emulsion containing 1.3 parts of the sodium salt of a disproportionated wood rosin, 0.53 part of solid sodium hydroxide, 0.4 part of the sodium salt of a condensation product of formaldehyde and naphthalenesulfonic acid, and 0.3% of sodium bisulfite based on the weight of the chloroprene. Dodecyl mercaptan is the modifying agent and is used in an amount of about 0.23% based on the weight of the chloroprene. The polymerization catalyst is a solution of 0.3% potassium persulfate and 0.015% of sodium anthraquinone-β-sulfonate. This preparation follows the teachings of Example 6 of U.S. 2,494,087.
[b]Sold as "Circo" LP oil by Sun Oil Co.
[c]Octylated diphenylamine, sold as "Antox" N by E. I. du Pont de Nemours and Co.
[d]Sold as "Conac" S by E. I. du Pont de Nemours and Co.

The antiozonants have the following compositions:

I: 5-norbornene-2-methanol 10%, bis(5-norbornene-2-methyl) phosphite 90%.
II: 5-norbornene-2-methanol 0.42%, tris(5-norbornene-2-methyl) phosphate 95.2%, tris(5-norbornene-2-methyl) phosphite 0.82%.
III: 5-norbornene-2-methanol 5.8%, bis(5-norbornene-2-methyl) phosphite 15.9%, tris(5-norbornene-2-methyl) phosphite 65.5%, tris(5-norbornene-2-methyl) phosphate 0.7%.

The tensile properties were determined according to ASTM method D-412-68.

The antiozonant effect was measured by exposing cured samples to ozone in a test chamber at 40° C. using an ozone concentration of 3 parts per million. For static exposures, samples of the vulcanizates 0.25 × 0.075 × 6 inches in dimension, mounted on varnished wooden racks, were subjected to tensile strains of 40 percent. The dynamic tests were carried out by the "roller" method described in *Rubber Chemistry and Technology* 32, 1119 (1959). The test pieces were flexed at a rate of 30 cycles per minute. The number of hours required to produce a given degree of cracking was observed.

The following results were obtained.

TABLE I

| Sample | 1 | 2 | 3 | 4 |
|---|---|---|---|---|
| antiozonant | none | I | II | III |
| Parts | — | 2.4 | 2.28 | 2 |
| Norbornene Content (Parts) | — | 1.55 | 1.47 | 1.21 |
| Stress-Strain Properties | | | | |
| (Press Cure, 30 Min./153° C.) | | | | |
| Shore A Hardness | 42 | 36 | 37 | 37 |
| 300% Modulus, psi | 640 | 500 | 440 | 495 |
| Tensile Strength, psi | 2190 | 1480 | 1760 | 1610 |
| Elongation, % | 580 | 540 | 640 | 555 |
| Ozone Resistance | | | | |
| Static (40% Elongation), 3 ppm at 40° C. | | | | |
| Original (Hrs. to Break) | 43.5 | >127 | >127 | >127 |
| Aged 7 Days/100° C. (Hrs. to Break) | 37.5 | >232 | >232 | >232 |
| Dynamic, 0.5 ppm at 40° C. | | | | |
| Original (Hrs. to Bad Cracking) | 41 | 96 | 54 | 96 |
| Aged 7 Days/100° C. (Hrs. to Bad Cracking) | 13 | 39.5 | 95.5 | >95.5 |

I claim:
1. Bis(5-norbornene-2-methyl) phosphite.
2. Tris(5-norbornene-2-methyl) phosphite.
3. Tris(5-norbornene-2-methyl) phosphate.
4. A composition of matter consisting essentially of a mixture of bis(5-norbornene-2-methyl) phosphite, tris(5-norbornene-2-methyl) phosphite, tris(5-norbornene-2-methyl) phosphate, and 5-norbornene-2-methanol; the weight proportion of tris(5-norbornene-2-methyl) phosphite being at least about 41%.
5. A composition of matter of claim 4 wherein the proportion of tris(5-norbornene-2-methyl) phosphite is at least about 65%.
6. A composition of matter of claim 4 wherein the proportion of tris(5-norbornene-2-methyl) phosphite is at least about 80%.
7. A composition of matter consisting essentially of a mixture of bis(5-norbornene-2-methyl) phosphite, tris(5-norbornene-2-methyl) phosphite, tris(5-norbornene-2-methyl) phosphate, and 5-norbornene-2-methanol.
8. A composition of matter consisting essentially of a mixture of bis(5-norbornene-2-methyl) phosphite, tris(5-norbornene-2-methyl) phosphite, and tris(5-norbornene-2-methyl) phosphate.

* * * * *